United States Patent
Hristov et al.

(10) Patent No.: US 9,636,210 B2
(45) Date of Patent: May 2, 2017

(54) INJECTION ZONE MARKERS FOR BIOMEDICAL IMPLANTS

(71) Applicant: Mentor Worldwide LLC, Santa Barbara, CA (US)

(72) Inventors: Krasimira Hristov, Belle Mead, NJ (US); Leo B. Kriksunov, Ithaca, NY (US); Robert J. Tannhauser, Bridgewater, NJ (US)

(73) Assignee: Mentor Worldwide LLC, Irvine, CA (US)

( * ) Notice: Subject to any disclaimer, the term of this patent is extended or adjusted under 35 U.S.C. 154(b) by 102 days.

(21) Appl. No.: 14/280,864

(22) Filed: May 19, 2014

(65) Prior Publication Data

US 2015/0327985 A1      Nov. 19, 2015

(51) Int. Cl.
*A61F 2/12* (2006.01)
*A61B 8/08* (2006.01)

(52) U.S. Cl.
CPC ............... *A61F 2/12* (2013.01); *A61B 8/481* (2013.01); *A61F 2250/0069* (2013.01); *A61F 2250/0098* (2013.01)

(58) Field of Classification Search
CPC ....................................................... A61F 2/12
See application file for complete search history.

(56) References Cited

U.S. PATENT DOCUMENTS

| | | |
|---|---|---|
| 4,636,213 A | 1/1987 | Pakiam |
| 4,805,628 A | 2/1989 | Fry et al. |
| 4,863,470 A | 9/1989 | Carter |
| 6,203,570 B1 | 3/2001 | Baeke |
| 6,743,254 B2 | 6/2004 | Guest et al. |
| 7,702,378 B2 | 4/2010 | Bolan et al. |
| 8,320,993 B2 | 11/2012 | Sirimanne et al. |
| 8,382,723 B2 | 2/2013 | Powers et al. |
| 8,382,724 B2 | 2/2013 | Maniar et al. |
| 2003/0144734 A1 | 7/2003 | Dreschnack et al. |
| 2003/0149481 A1 | 8/2003 | Guest et al. |
| 2004/0073107 A1 | 4/2004 | Sioshansi et al. |

(Continued)

FOREIGN PATENT DOCUMENTS

| | | |
|---|---|---|
| WO | WO 98/19713 A1 | 5/1998 |
| WO | WO 03/034894 A2 | 5/2003 |

(Continued)

OTHER PUBLICATIONS

Couture et al.: "Reflection from Bound Microbubbles at High Ultrasound Frequencies"; IEEE Transactions on Ultrasonics, Ferroelectrics and Frequency Control, (2009), pp. 536-545, vol. 56(3).

*Primary Examiner* — Katrina Stransky
*Assistant Examiner* — Wade P Schutte (57) ABSTRACT

A mammary implant and method of making are provided herein. The implant includes an outer shell configured to retain fluid therein, an injection element coupled to the outer shell and adapted to receive therethrough an injection device for injecting fluid into the outer shell, and an injection marker zone made of a material having ultrasonically detectable markers incorporated therein. The markers are a plurality of microcavities that are located relative to the injection element so that, when ultrasonically detected, such detection indicates a location of the injection element.

12 Claims, 12 Drawing Sheets

(56) References Cited

U.S. PATENT DOCUMENTS

| | | |
|---|---|---|
| 2004/0093069 A1 | 5/2004 | Priewe et al. |
| 2005/0033157 A1 | 2/2005 | Klein et al. |
| 2006/0264898 A1 | 11/2006 | Beasley et al. |
| 2010/0198057 A1 | 8/2010 | Kerr et al. |
| 2011/0230964 A1 | 9/2011 | Yacoub et al. |
| 2011/0275930 A1 | 11/2011 | Jho et al. |
| 2012/0165934 A1* | 6/2012 | Schuessler ............... A61F 2/12 623/8 |
| 2014/0277440 A1* | 9/2014 | Martin ..................... A61F 2/12 623/8 |
| 2015/0305853 A1* | 10/2015 | Schuessler ............... A61F 2/12 623/8 |

FOREIGN PATENT DOCUMENTS

| | | |
|---|---|---|
| WO | WO 03/034894 A3 | 5/2003 |
| WO | WO 2011/084465 A2 | 7/2011 |
| WO | WO 2011/084465 A3 | 7/2011 |
| WO | WO 2011/140217 A1 | 11/2011 |

* cited by examiner

INJECTION ZONE MARKERS FOR BIOMEDICAL IMPLANTS

BACKGROUND OF THE INVENTION

The present invention relates to implantable devices, and more particularly to tissue expanders and prostheses having markers to assist in locating the implant or selected area(s) of the implant once implanted. Although the tissue expanders may be used in other areas of the body, one specific application is mammary implants such as soft tissue expanders.

Tissue expanders are devices that are implanted beneath the skin or muscle and then gradually inflated to stretch the overlying tissue. Expanders are commonly used either to create a pocket for receiving a permanent prosthesis, or to generate an increased skin surface area in anticipation of the new skin being utilized for grafting or reconstruction.

Conventional implantable mammary tissue expanders are formed of a silicone polymer shell. After implantation, a fluid, such as saline, is periodically injected into the expander to enlarge it over time. Between injections, the surrounding skin is permitted to stretch and grow to create the increased skin surface and the increased tissue pocket for receipt of the permanent implant. Typically, a tissue expander will be provided with an injection element through which fluid can be introduced into or withdrawn from the expander. One such injection element is an integrated injection dome comprising a septum that can be pierced with a hypodermic needle for the introduction into or withdrawal of fluid from the expander. Alternatively, the injection element may be a self-sealing area on the tissue expander which allows penetration by a hypodermic needle and self-closing after the withdrawal of the needle.

It can be difficult, however, to accurately locate the injection element through the overlying tissue once the expander has been implanted. If the injection element is missed and the needle punctures the shell of the tissue expander, the expander can leak, which typically requires removal and replacement of the expander. In an effort to reduce the likelihood of inadvertent puncture, one known device provides an injection element surrounded by a self-sealing member, which provides a safety zone around the injection element. This type of arrangement is disclosed, for example, in the U.S. Pat. No. 6,743,254, the disclosure of which is hereby incorporated by reference herein. Other solutions include providing a palpation ring around the injection element. It still can be difficult, however, to identify the proper location through tissue, and a raised palpation ring may cause additional pain and discomfort to the patient. Other known expanders use a magnetic component near or around the injection dome (such as sealing ring) or behind the dome (such as a needle stop). A detection device is then utilized to locate the magnetic component through interaction with the magnetic field. Yet other known devices have used radiographic detection of the access port, such as is disclosed in U.S. Pat. Nos. 8,382,723 and 8,382,724 and U.S. Patent Publication Nos. 2006/0264898 and 2010/0198057.

U.S. Patent Publication No. 2011/0275930, entitled "SYSTEMS AND METHODS FOR IDENTIFYING AND LOCATING AN IMPLANTED DEVICE", discloses a system for identifying an attribute of an implanted medical device, such as an access port. In one embodiment, the identification system includes a marker and an external detection device with a signal source that emits an incident electromagnetic signal for impingement on the marker and a detector that detects a return signal from the marker, and a user interface for conveying information relating to the attribute based on detection of the return signal. In the case of an implantable access port, for instance, the described system enables information, such as the ability of the port to withstand power injection of fluids therethrough, to be ascertained even after the port has been subcutaneously implanted within the patient.

Systems and methods of the types described above are not ideal. Magnetic field based detection systems incorporate magnets or metallic parts, which may be undesirable to some patients, and which result in difficulties in passing through airport security or undergoing MRI procedures, etc. Radiographic detection systems require additional exposure to radiation, which is undesirable. Further, these types of devices require additional parts, which add to the cost of the expander itself. Thus, there is a need to provide an implant including an improved marker for more readily locating the implant once implanted.

BRIEF SUMMARY OF THE INVENTION

The present invention provides a mammary implant including an outer shell configured to retain a fluid therein, an injection element coupled to the outer shell and adapted to receive therethrough an injection device for injecting fluid into said outer shell, and an injection marker zone made of a material having ultrasonically detectable markers incorporated therein. The markers are a plurality of microcavities that are located relative to the injection element so that, when ultrasonically detected, such detection indicates a location of the injection element.

In one embodiment, the microcavities each have a size less than or equal to 200 microns. The microcavities may be filled with gas, and in alternate embodiments the gas may be air, nitrogen, carbon dioxide, or argon.

In yet another embodiment, the microcavities are substantially uniformly distributed within the material, and/or may have a density of at least 1000 microcavities per $cm^2$.

The injection marker zone may be configured to substantially surround the injection element, may have a substantially circular outer shape, or may have a substantially rectangular outer shape.

In yet another alternate embodiment, the injection marker zone overlays at least a portion of said injection element. Alternatively, it may form part of the outer shell, with the plurality of microcavities incorporated within the shell. Further, the shell may be made of silicone.

In yet another embodiment, the injection marker zone forms part of the injection element, and the microcavities are embedded within a material forming at least a part of the injection element.

The present invention also provides an inflatable implant including an outer shell configured to retain fluid therein, an injection element coupled to the outer shell and adapted to receive therethrough an injection device for injecting fluid into the outer shell, and an injection marker zone positioned relative to the injection element so as to identify a location of the injection element. The injection marker zone is made of a material having incorporated therein a plurality of gas filled microcavities each having a size less than or equal to 200 microns.

Also provided herein is a method of making an implant having an ultrasonically detectable injection marker zone. The method includes the steps of forming an outer shell of the implant that is made of a flexible material, coupling to the flexible outer shell an injection element adapted to receive therethrough an injection device for injecting fluid into the outer shell, preparing a liquid material having a plurality of microcavities suspended therein, wherein the microcavities are gas filled and have a size less than or equal to 200 microns, and applying the liquid material having the plurality of microcavities suspended therein to the implant at a predetermined location to form an injection marker zone, wherein the injection marker zone identifies a relative location of the injection element when ultrasonically detected.

In one embodiment, the preparing step further includes injecting a gas into the liquid material through an injector or sparger having a plurality of orifices having size less than or equal to 200 microns.

In yet another embodiment, the preparing step further includes using a high speed agitator to agitate the liquid material in the presence of gas. In yet another alternate embodiment, the preparing step further includes dispersing preformed gas filled microcapsules into the liquid material.

In yet another embodiment, the outer shell and injection marker zone are made of silicone.

These and other objects, features and advantages of the present invention will be apparent from the following detailed description of illustrative embodiments thereof, which is to be read in connection with the accompanying drawings.

DETAILED DESCRIPTION

In the following are described various embodiments of a mammary implant, such as a mammary tissue expander, with markers according to the present invention. Where like elements have been depicted in multiple embodiments, identical or similar reference numerals have been used for ease of understanding.

As indicated, the present invention relates to implants having markers for more readily detecting the location of the implant, or portions thereof, once implanted within a patient. Exemplary implants having such markers will first be generally described below, followed by a more detailed description of the markers themselves and various methods for integrating such markers into implants, and methods for their use.

The invention described below leverages the general, well known concept that the difference between solid or liquid vs. gas can be detected by ultrasound. It is further known that small air bubbles on a gelatin surface can be detected by ultrasound within limits. See "Reflection from Bound Microbubbles at High Ultrasound Frequencies", by Olivier Couture, et al., published in IEEE Transactions on Ultrasonics, Ferroelectrics and Frequency Control, Vol. 56, Issue 3, pp. 536-545 (2009). The present invention provides a novel and inventive medical device that utilizes microbubbles or microcavities to readily locate an injection port or injection zone in a mammary expander, that is simple and cost effective to manufacture, that does not require additional devices or parts, and that does not adversely affect the structural integrity of the device itself.

Figure 1A:
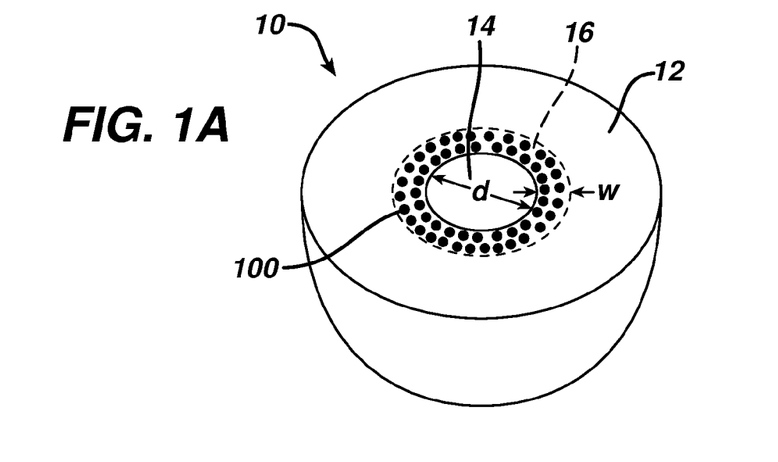
FIGS. 1A-1B are perspective and top views respectively of an exemplary mammary tissue expander according to the present invention.
Figure 1B:
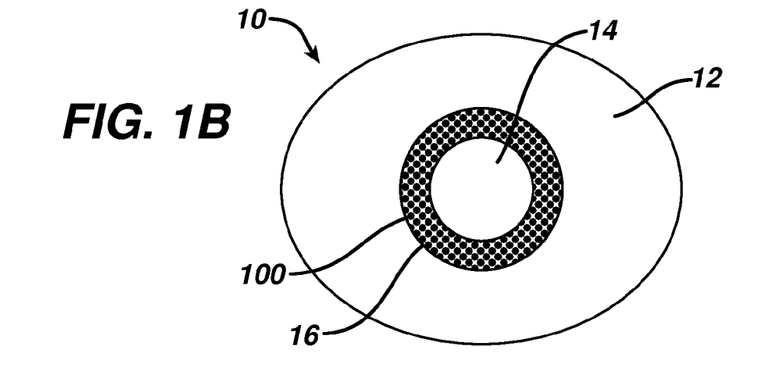
Figure 1C:
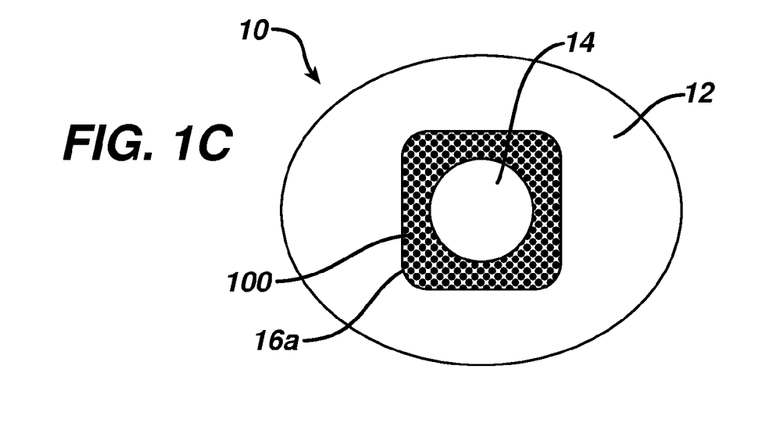
FIG. 1C is a top view of an alternate embodiment of a mammary tissue expander according to the present invention.

Referring first to FIGS. 1A-1C, an exemplary mammary tissue expander 10 is shown having an outer shell 12, preferably made of a cross-linked silicone elastomer, and an injection element 14 such as an injection dome through which an injection device, such as a syringe (not shown), is used to add or remove fluid from the outer shell 12 to adjust the shell's volume in a manner well known in the art.

An injection marker zone 16 helps identify the injection dome 14 through the tissue by providing a plurality of markers 100 which will be described in more detail below. In the embodiment shown in FIGS. 1A and 1B, the markers 100 are arranged immediately around injection dome 14 so that the injection marker zone has an overall shape of a ring. Injection dome 14 can be readily located in the center by detecting the injection marker zone 16, as will also be described more fully below. The width w of injection marker zone 16 is selected for easy detection, and preferably is from 10% to 100% of the diameter of dome 14, and more preferably from 20% to 40% of the diameter dome 14. In one embodiment, the injection marker zone is from 3 mm to 20 mm wide, and more preferably 10 mm wide. FIG. 1C depicts an embodiment of tissue expander 10 with the injection marker zone 16a having generally rectangular outer shape. Although particular configurations of the injection marker zone are shown and described herein, it is to be understood that any suitable shape and configuration may be used in accordance with the present invention so long as the injection marker zone may be readily detected, and the injection element located based on such detection.

Figure 2:
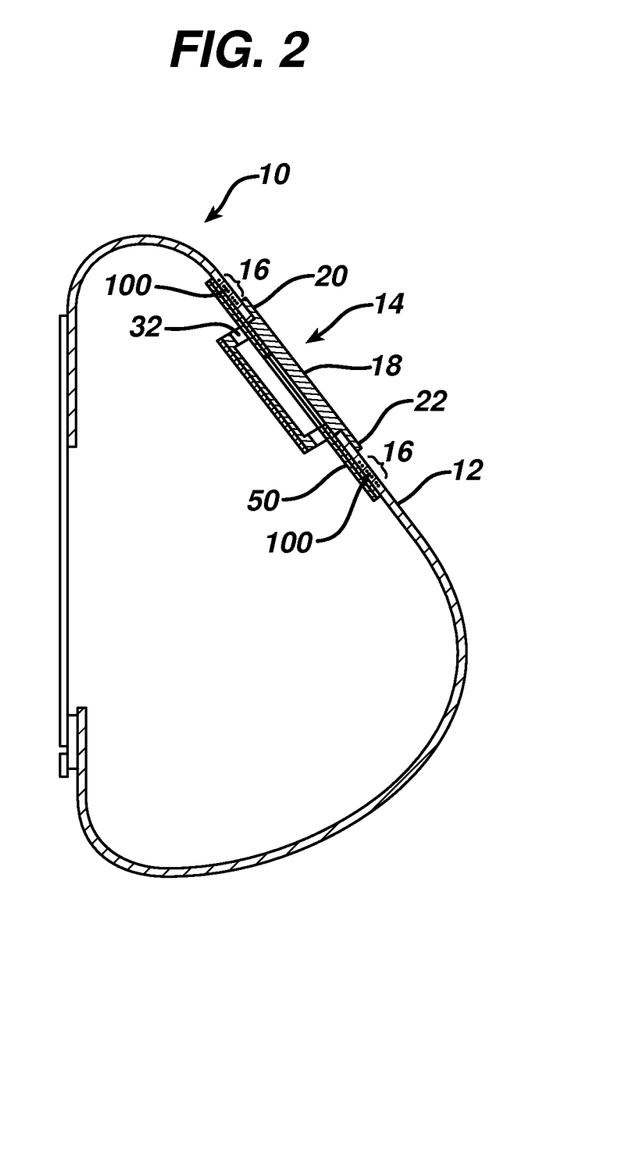
FIG. 2 is a cross-sectional, side view of the tissue expander of FIG. 1.
Figure 3:
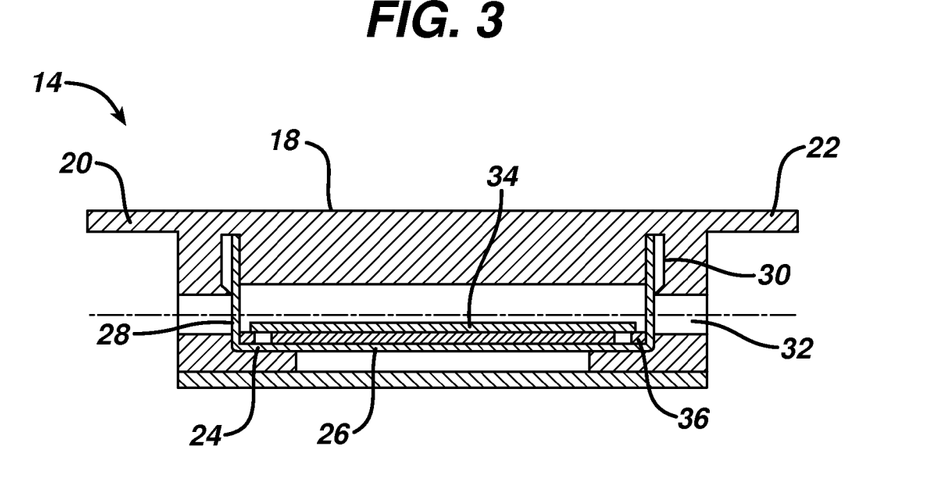
FIG. 3 is a cross-sectional, side view of an exemplary injection dome that may be used in conjunction with the present invention.

FIG. 2 is a cross-sectional, side view of an exemplary mammary tissue expander 10 including an outer shell 12 with an injection dome 14. Injection marker zone 16 is shown with markers 100 incorporated directly into the shell 12 in the area around the injection dome 14. Also shown is an optional reinforcing area or optional self-sealing safety patch area 50 formed around the exemplary injection dome 14. FIG. 3 is a cross-sectional view of the exemplary injection dome 14 of FIG. 2 showing additional details thereof. As indicated, the function of the injection dome 14 is to allow controlled introduction and/or removal of fluid from the tissue expander 10. Generally, this is accomplished through use of a hypodermic needle or syringe (not shown) that pierces a selected region of the injection dome 14, such as septum region 18 which may be formed of elastomeric material.

In the illustrated embodiment, the injection dome 14 is fitted into an opening in the outer shell 12, for example at a location intended to face the skin of the patient to be expanded. The casing 20 of the injection dome is typically formed of an elastomeric material. The septum region 18 of the casing 20 is preferably located at the central region of the upper surface of the casing. The septum region 18 is self-sealing, preventing the leaking of fluid from the implant 10 after removal of the hypodermic needle from the injection dome. A flange 22 extends around the upper edge of the dome casing 20, and overhangs the shell 12, which is partially sandwiched between the flange and the optional self-sealing safety patch 50. As the flange 22 rests against the outer surface of the shell 12, it provides a surface for securely attaching the assembled injection dome 14 to the shell. In order to prevent accidental puncture of the shell 12 through the injection dome 14 itself, the injection dome is equipped with an optional needle guard 24 which functions as a backstop for the needle. The rim portion 28 of the needle guard is fitted into an annular slot 30 in the underside of the dome casing 20. When the needle guard 24 is inserted into the slot 30 in the injection dome 14, compressive force is exerted on the elastomeric material of the septum region 18 of the injection dome 14. As a result of these forces, the septum region 18 of the injection dome 14 is self-sealing. Openings 32 in the rim portion 28 of the needle guard 24 allow fluid to pass to the interior of the shell 12. A needle damper 34, preferably formed of a resilient material, e.g., polysulfone, is positioned on top of the base 26 of the needle guard 24 to prevent damage to the hypodermic needle tip should the needle be inserted so far as to actually strike the needle guard. It is prudent to reduce the risk of damage to the hypodermic needle because a bent tip could tear a non-repairable hole that compromises the self-sealing capability in the septum region 18 upon withdrawal of the needle from the injection dome 14. The needle damper 34 is preferably adhesively fastened to the needle guard 24. The outer shell 12 of the tissue expander can have any desired shape and any thickness that is suitable for the purpose of the particular expander. The shell is commonly formed of a biocompatible elastomer such as silicone.

Dip molding using an appropriately sized and shaped mandrel can be used to form the outer shell 12, although other suitable means such as injection molding or spraying may also be used. With dip molding, the mandrel is dipped into silicone dispersion and then removed to allow for partial cure and solvent evaporation. The process is generally repeated several times. Once the outer shell 12 has been formed it is removed from the mandrel. This dip molding process results in the formation of a partial shell that has an opening, e.g., a circular hole (patch hole), on the posterior side. The injection dome 14 is installed and the patch hole is subsequently covered with a patch that seals the hole, thus forming a complete, fluid impervious shell. The patch is attached to the partial shell using silicone rubber or other similar biocompatible adhesive. The completed shell can either be non-filled or partially prefilled. After implantation, the expander 10 is intraoperatively filled through the septum region 18 with saline, gel, foam, or combinations of these materials or other suitable materials known in the art to gradually expand the tissue expander to the desired dimensions. This typically takes place over the course of multiple office visits.

Figure 4A:
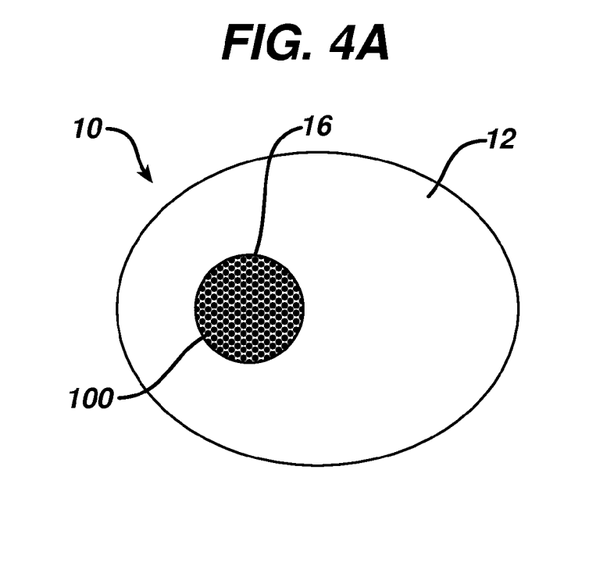
FIG. 4A is a top view of an alternative embodiment of a mammary tissue expander according to the present invention.
Figure 4B:
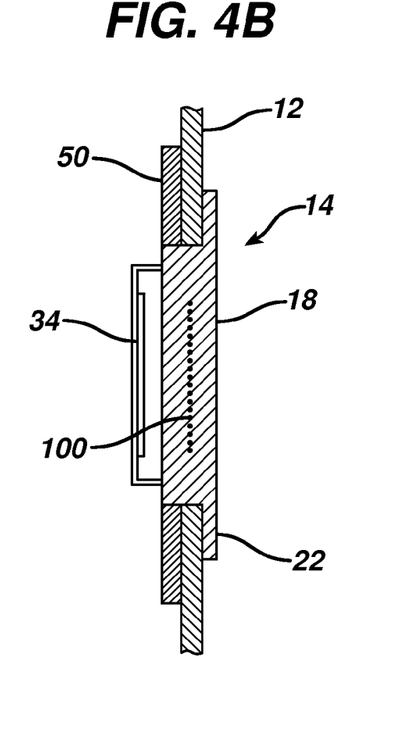
FIG. 4B-4C are cross-sectional views of various exemplary embodiments of an injection dome having markers incorporated therein.
Figure 4C:
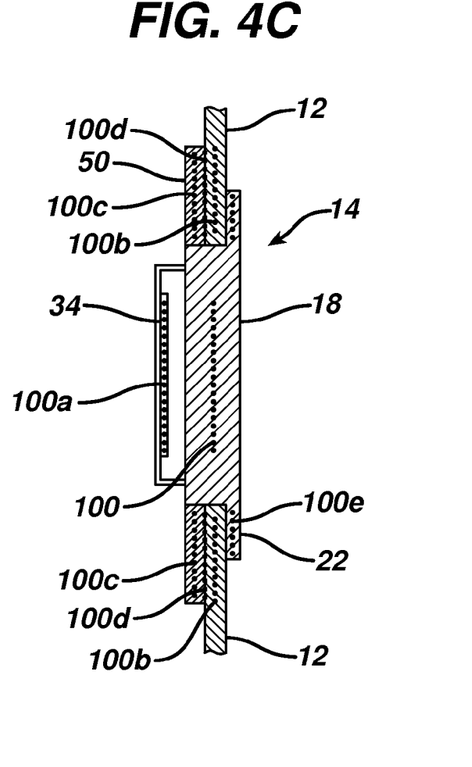

Referring now to FIG. 4A, an alternate embodiment of tissue expander 10 is shown with markers 100 incorporated directly into the body of injection dome 14 itself, and preferably into septum region 18. Markers 100 can be embedded throughout septum region 18 or form any geometric shape within the septum region 18 which enables a surgeon to identify it postoperatively. FIG. 4B shows a schematic cross-sectional view of one embodiment of an injection dome 14 and outer shell 12 in the vicinity of injection dome 14, with markers 100 embedded into the septum region 18. FIG. 4C illustrates various alternate areas where markers 100 can be embedded, such as throughout septum region 18, into needle damper 34, into outer shell 12 around injection dome 14, into optional reinforcing area or optional self-sealing safety patch area 50, at the interface between optional reinforcing area or optional self-sealing safety patch area 50 and outer shell 12, or into flange 22. In certain embodiments, markers in the same tissue expander are embedded into more than one area. It is to be understood that the markers described more fully below can be embedded in any suitable area and in any suitable configuration so long as sufficient to enable identification of the location of the injection element.

Figure 5A:
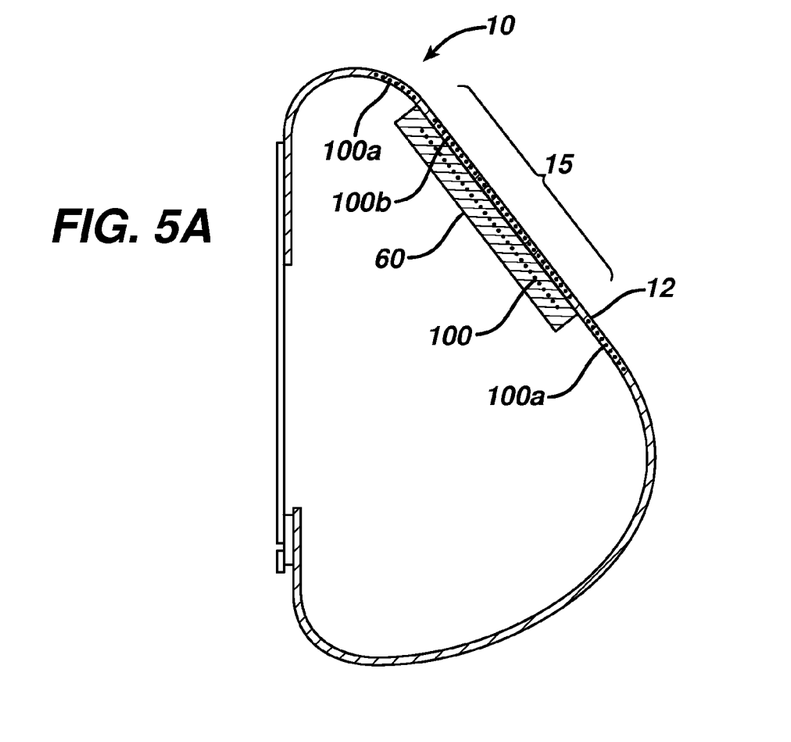
FIG. 5A is a cross-sectional, side view of yet another embodiment of a mammary tissue expander according to the present invention.
Figure 5B:
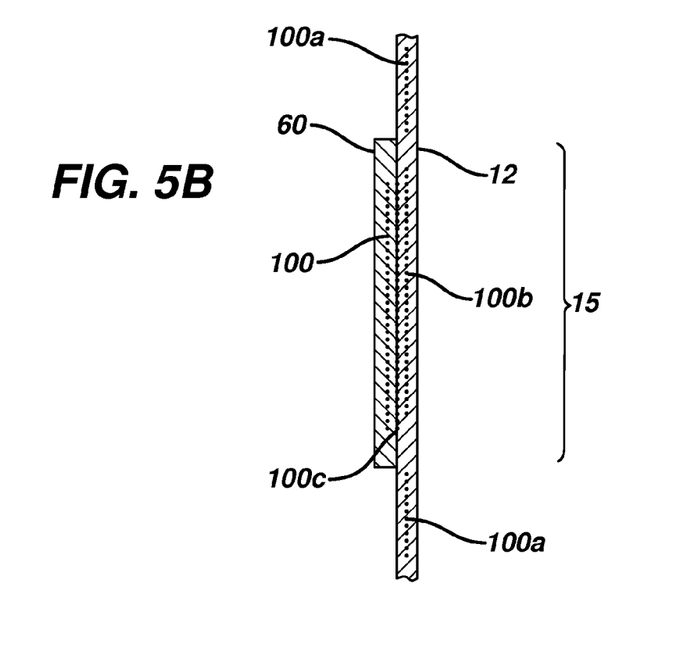
FIG. 5B is an alternative embodiment of a self-sealing structure having markers according to the present invention.

The markers of the present invention can also be used in tissue expanders that do not have an injection dome, but instead have a self-sealing zone 15 formed of a self-sealing material or self-sealing structure 60, as known in the art. Referring now to FIGS. 5A and 56, the self-sealing structure 60 may be attached to outer shell 12 from the inside as illustrated. Injections are performed through self-sealing zone 15, which is localized by markers 100 of the present invention. These markers may alternatively be embedded into outer shell 12 around the self-sealing structure 60 (100a), into outer shell 12 in the area overlaying the self-sealing structure, or at the interface between outer shell 12 and self-sealing structure 60. In certain embodiments, markers in the same tissue expander 10 are embedded into more than one area.

Figure 6A:
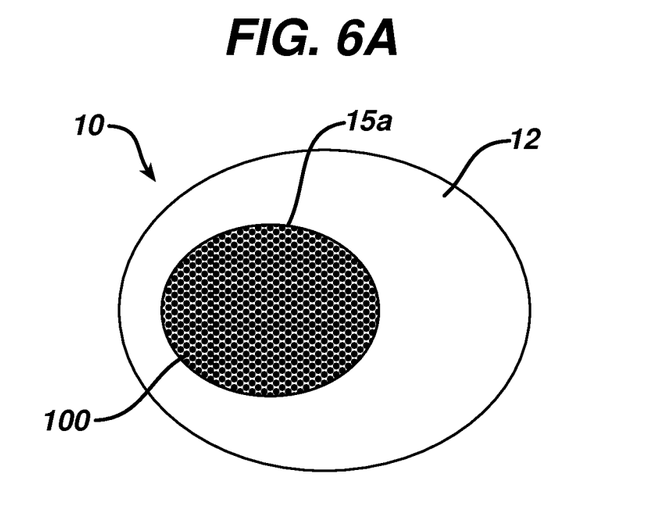
FIGS. 6A-6B and 7A-7B illustrate various configurations and locations for injection marker zones.
Figure 6B:
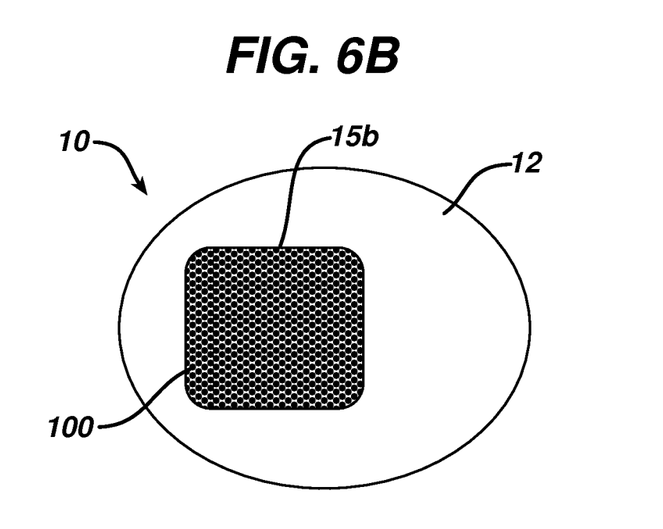
Figure 7A:
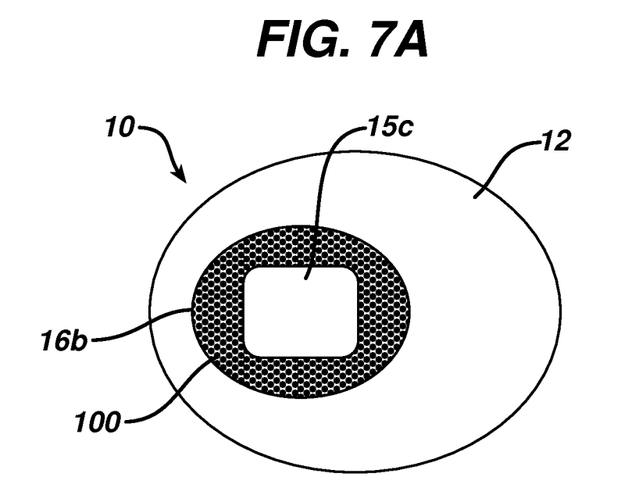
Figure 7B:
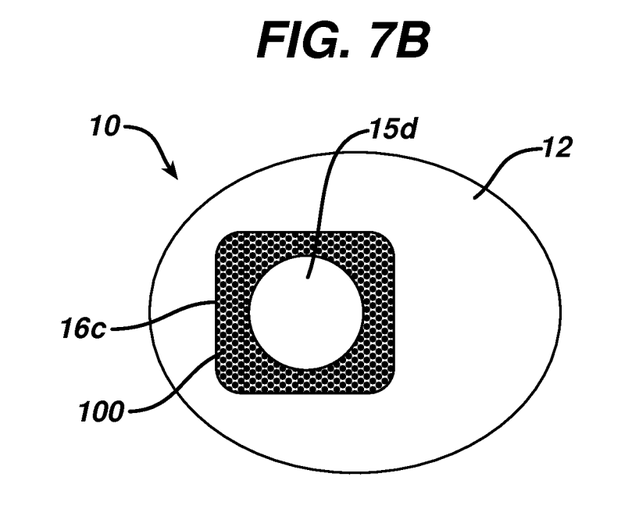

The markers 100 may be embedded into the self-sealing structure 60 in any suitable configuration such as an overall oval form as shown in FIG. 6A or an overall rectangular form as shown in FIG. 6B. Alternatively, the markers 100 may be embedded into outer shell 12 around the self-sealing zone 15c, 15d in any suitable configuration or shape, for example as shown in FIGS. 7A and 7B.

The markers 100 of the present invention will now be described in more detail with reference to FIGS. 8-11. The markers are a plurality of microcavities embedded directly into specific areas of the implant such as those areas described above. The microcavities are defined herein as any small compartments formed directly within a material of the applicable implant, including gas or vacuum filled microbubbles, micropockets, microvoids. In each instance the microcavities are readily detectable by ultrasound, and are sized (maximum dimension or in the case of spherical microbubbles, outer diameter) within the range of about 0.1 micron to about 500 microns, and more preferably 0.5 micron to 200 microns, even more preferably 1 micron to 100 microns, and most preferably 1 micron to 25 microns. According to certain embodiments of the present invention, there are at least 100 microcavities per $cm^2$, more preferably at least 1000 microcavities per $cm^2$, most preferably at least 10000 microcavities per $cm^2$. Typically the microbubbles are spherical, but they can also be ellipsoidal.

Advantageously, these microcavities are readily formed directly in the structures of the implant, with no additional separate structures needed to enable detection as is the case with known mammary tissue expanders. Also, due to the small size of the microcavities, the strength of the material is not compromised and the self-sealing property of the material, if any, is not compromised.

Figure 8A:
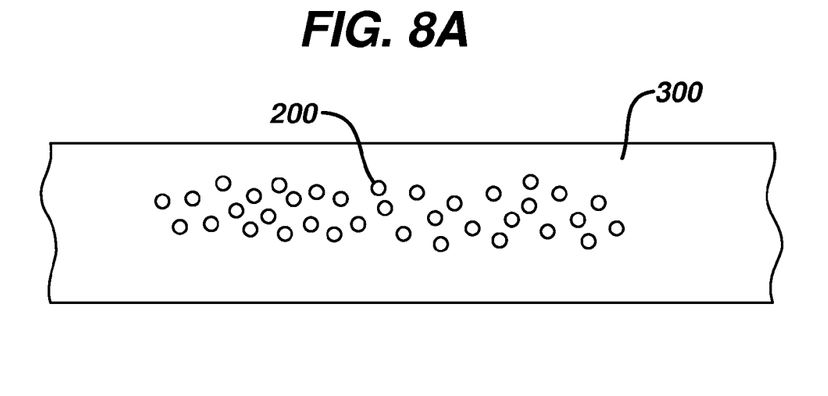
FIGS. 8A-8B illustrate various arrangements for injection marker zones according to the present invention.
Figure 8B:
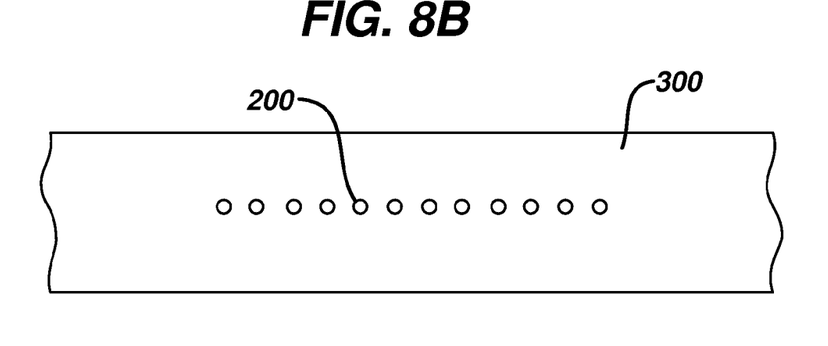
Figure 9:
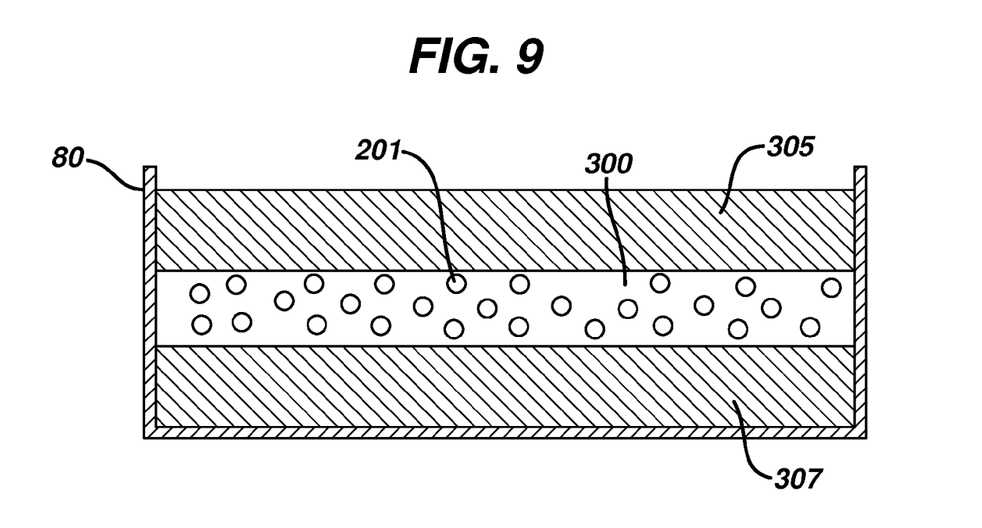
FIG. 9 illustrates one embodiment of a layered structure having markers embedded therein.

FIGS. 8A and 8B show embodiments of any suitable material (i.e., such as a silicone based polymeric material for mammary tissue expanders) with multiple microcavities 200 embedded therein. The microcavities may be in any suitable configuration, such as the somewhat random pattern shown in FIG. 8A, or aligned as shown in FIG. 8B. Advantageously, the configuration shown in FIG. 8A provides for higher density of microcavities which can be positioned as shown, arranged throughout the thickness of the material, or in a multilayer arrangement.

According to one embodiment, microcavities 200 are formed in the material 300 from microbubbles of gas which are suspended in a liquid or semi-liquid polymer which is a precursor to solid material 300. This can be accomplished by injecting a gas into the liquid polymer through an injector or sparger having one or more fine orifices, thus forming a suspension of fine microbubbles in the liquid polymer. Alternatively, a high speed impeller can be used to agitate liquid polymer in the presence of gas, such as air or nitrogen, forming a dispersion of fine microbubbles within the liquid polymer.

Other means include applying a vacuum treatment to a liquid polymer having dissolved gas therein, or applying a high pressure gas atmosphere to a liquid polymer for a period of time that allows the gas to partially dissolve in the liquid polymer, where after the pressure is removed, excess dissolved gas will form a dispersion of fine microbubbles within the liquid polymer.

Still another method of forming a suspension of microbubbles in a liquid or semi-liquid polymer is by dispersing gas-filled microcapsules in the liquid or semi-liquid polymer, for instance by adding a quantity of polymer-shell gas-filled microcapsules to the liquid or semi-liquid polymer and mixing the microcapsules into the bulk of the liquid. Alternatively, polymer-shell microcapsules can be added on top of a still liquid layer of polymer being cast in a suitable form while the polymer is being cured, resulting in a uniform layer of microcavities 200 formed by gas-filled microcapsules.

Another method of forming a suspension of microbubbles in the liquid or semi-liquid polymer, is directional application of high energy ultrasound, or sonication, whereby due to cavitation processes and/or due to changes in gas solubility, formation of microbubbles can be induced within the liquid or semi-liquid polymer.

Yet another method of forming a suspension of microbubbles in the liquid or semi-liquid polymer, is directional application of high energy laser energy, whereby due to thermal effects, formation of microbubbles can be induced within the liquid or semi-liquid polymer.

Figure 10:
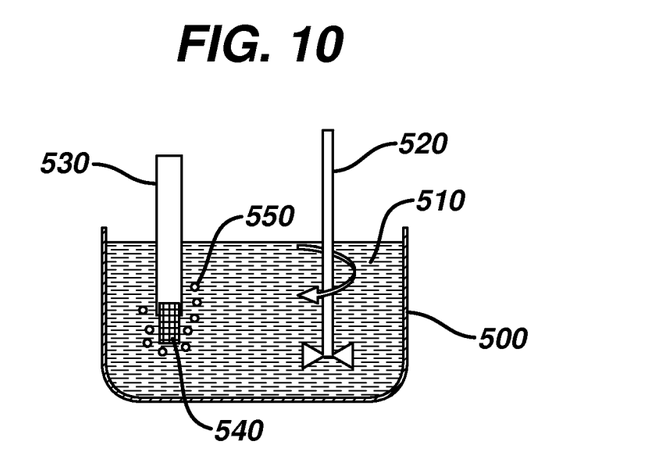
FIG. 10 illustrates one exemplary means by which to form a suspension of microbubbles or microcavities in a liquid.

One method of forming a suspension of microbubbles in the liquid polymer is schematically illustrated in FIG. 10, which shows in a cross-sectional view, a container 500 containing liquid polymer 510 and an optional agitator, such as a stirrer, impeller or the like 520. Pressurized gas is supplied via gas line 530 and is injected into liquid polymer 510 through a microporous sparger 540, such as a sintered glass, polymer, or metal frit, having pores of the order of 0.5 microns to about 20 microns, such as 1 micron or 2 microns. Injection of the gas into the liquid polymer 510 forms microbubbles 550 suspended or dispersed within the liquid polymer.

Figure 11A:
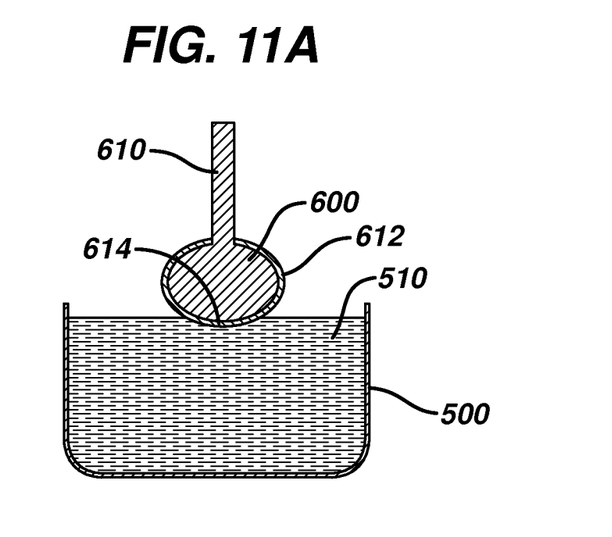
FIGS. 11A-11E illustrate various aspects of various exemplary means by which to incorporate liquid having a suspension of microcavities or microbubbles therein into or onto a mammary tissue expander.
Figure 11B:
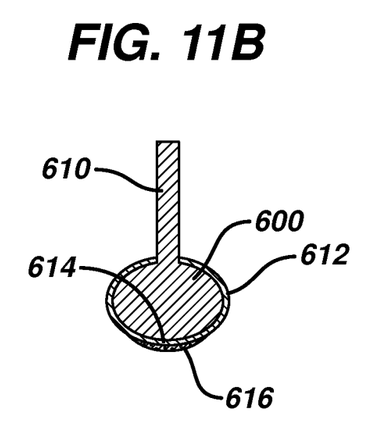

After a suspension of microbubbles is formed in the liquid polymer, a number of techniques can be used to incorporate the material (or liquid precursor to material) with embedded microcavities into a tissue expander or inflatable breast implant. As indicated previously, many breast implants and mammary expanders are formed of silicone using well known dip molding techniques. Following any curing step, the shell may be selectively dipped into a different vat of liquid silicone that contains microbubbles or microcavities as described above. The mandrel may be selectively dipped so that only a desired location (i.e., one that will identify the relative location of the injection element) is dipped. The shell may then be processed as usual, with additional dipping steps if desired using the original liquid silicone, to form the final implant or expander shell. This exemplary method is illustrated in FIGS. 11A-11B, wherein FIG. 11A shows mandrel 600 mounted on handle 610, with at least one or more layers of polymer already formed on the mandrel 600 and constituting the silicone shell 612. Mandrel 600 is subsequently partially dipped into a vat or container 500 containing liquid polymer 510 with microcavities 550 dispersed therein, so that only area 614 representing a portion of shell 612 is immersed into liquid polymer 510. Area 614 corresponds to the area where markers 100 of the present invention are desired to be placed (i.e., in the injection marker zone). The presence of microcavities or microbubbles 550 in polymer 510 is schematically illustrated by pattern coloring of polymer 510 in FIG. 11A.

After the mandrel 600 is withdrawn from the vat or container 500 and cured, the shell 612 now includes an additional layer 616 made of polymer with gas microbubbles dispersed therein as shown in FIG. 11B, forming the injection marker zone.

Figure 11C:
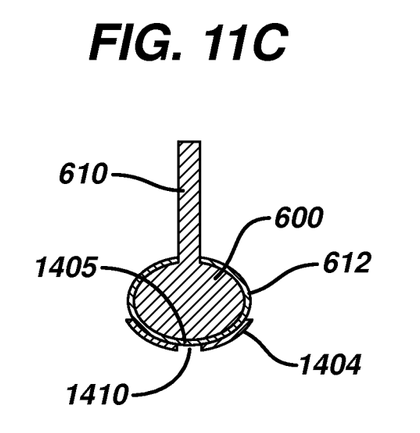
Figure 11D:
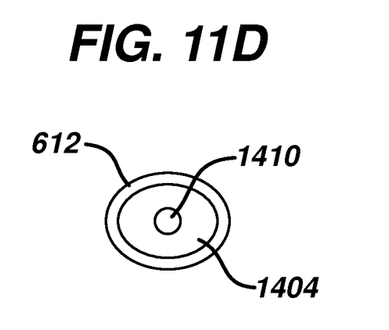
Figure 11E:
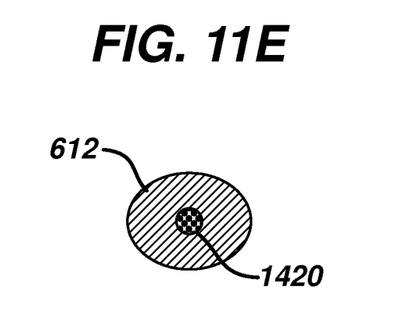

As an alternative to selective dipping of only a portion of the shell, well known masking techniques can be used to "mask off" locations other than the target location for the liquid silicon having microbubbles. An exemplary mask 1404 surrounding target location 1405 and having open area 1410 is shown in FIG. 11C in a cross-sectional view and in FIG. 11D in a top view. After application of the liquid silicon having microbubbles to shell 612, the area 1410 not covered by mask 1404 will form a coating of silicon having microbubbles dispersed therein. FIG. 11E is schematic top view of shell 612 of FIG. 11D after removal of the mask, showing injection maker zone 1420.

Alternate means for applying the liquid silicone with microcavities or microbubbles in the correct location include targeted spraying of the liquid with or without masking, or targeted application of the liquid by dropping or spreading the liquid on an already cured layer. The dispensing can be performed by using a micro-dispenser, pipette-like dispenser, liquid material printer, brush, ink-jet like spray deposition and the like, resulting in the formation of a layer made of polymer with gas microbubbles dispersed therein, thus forming an injection marker zone.

As indicated, subsequent layers of silicone without microbubbles can then be applied as desired. According to one illustrative embodiment shown in FIG. 9, a three-layer construct is cast in a form 80 with outside layers 305 and 307 being formed by a material having no microbubbles dispersed therein, with layers 305 and 307 sandwiching between them material 300 having microbubbles 201 dispersed therein. After casting and curing, a composite material with embedded microcavities is formed. Layers 305 and 307 can be made of the same material as layer 300, or of a different polymeric material.

According to the present invention, a specific gas other than air can be used to fill microcavities 200, such as nitrogen, carbon dioxide, argon, etc. Forming of cavities can be performed under specific gas atmosphere or specific gas can be used to inject into liquid polymer. Alternatively gas can be allowed to diffuse into cavities under elevated temperature and pressure over an extended period of time. In other embodiments, microcavities 200 are vacuum-filled, i.e., there is less than atmospheric pressure of any gas inside.

Figure 12A:
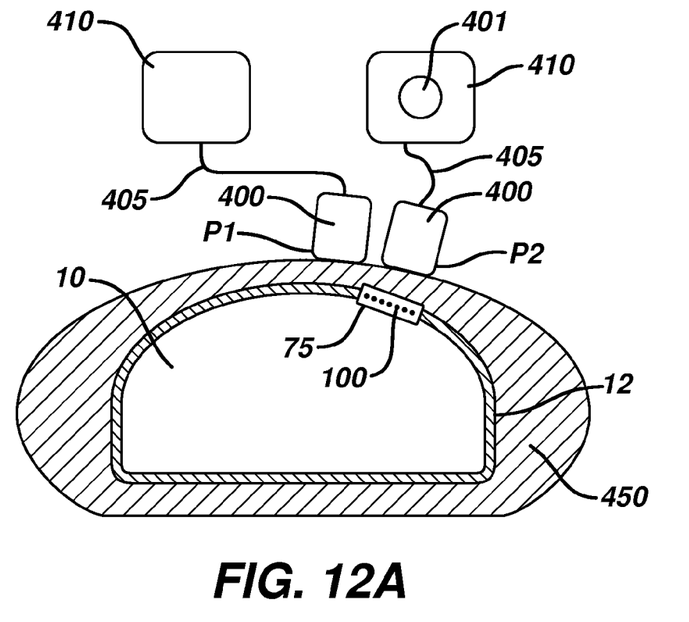
FIGS. 12A-12B and FIG. 13 illustrate exemplary uses of an implant according to the present invention in conjunction with a detection device.
Figure 12B:
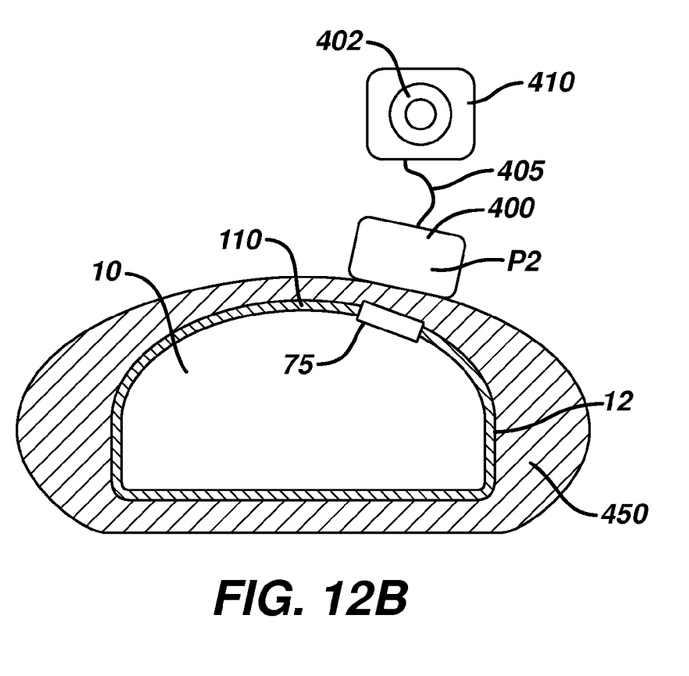

As indicated above, the microcavities are readily detectable using available ultrasonic instruments. For illustrative purposes, FIGS. 12A and 12B show a device having markers 100 according to the present invention in conjunction with such a detection device. A mammary tissue expander 10 is shown implanted into tissue 450, and which includes a shell 12 with an injection element 75 coupled to shell 12, with microcavities 100 embedded directly into and throughout the injection element 75. Ultrasonic detector 400 includes both a directional source of ultrasound and a receiver of reflected ultrasound, and is operatively connected to a visualization device 410, such as information display or monitor via cable 405. Ultrasonic detector 400 in position P1 which is not directly opposite the injection element 75 will detect no enhanced reflectance from microcavities 100, as schematically shown on visualization device 410. Ultrasonic detector 400 in position P2, which is directly opposite the injection element 75, will detect enhanced ultrasound reflectance from microcavities 100, as schematically shown on visualization device 410.

Referring now to FIG. 12B, tissue expander 10 includes microcavities 110 embedded around the injection element 75. In the position shown, ultrasonic detector 400 will detect enhanced reflectance from microcavities 110, as schematically shown on visualization device 410. Once its location is identified as described above, fluid for expanding the tissue expander 10 can be injected at the center of localized spot 401 or ring 402.

Alternatively, the ultrasonic detector may have no separate visualization display, but rather provides audible, visual, or vibratory feedback, or alternatively a combination of any two or all three of the above types of feedback, or any other additional modality of feedback or combinations of modalities of feedback. The ultrasonic detector may alternatively have a means to provide feedback, such as visual feedback from a built-in light source, such as one or more LED lamps, when detecting ultrasonic reflection from microcavities. Preferably, light output can change from one color, e.g., red, when there is no reflection; changing to a second color, such as to yellow, when reflection is stronger; and optionally changing to yet another color, such as green, when reflection is strongest. These types of devices are also well known in the art, and those skilled in the art will readily understand how to use them in conjunction with the present invention.

Figure 13:
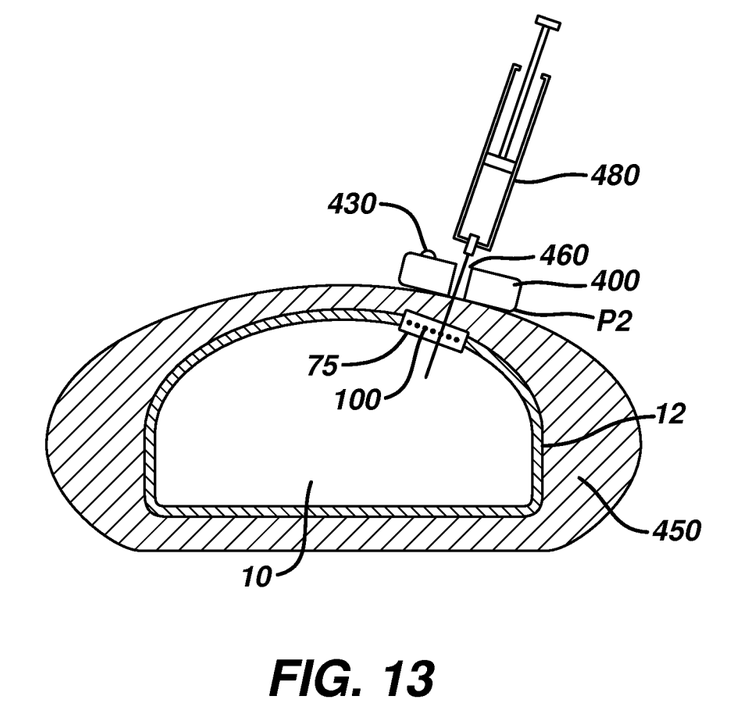

Once detector 400 has identified the position of markers 110, a health practitioner can optionally mark the area by using the position of detector 400. Referring to FIG. 13, in one embodiment, there is an aperture 460 within ultrasonic detector 400 through which the injection syringe 480 can be then placed. Alternatively, a pen can be used to mark the tissue through the aperture, or adjacent to the detector. Advantageously, as shown in FIG. 13 and also referring to FIGS. 4A, 6A and 6B, markers are embedded into the septum and the injection or withdrawal of fluid can be performed directly through the septum zone where markers are embedded. The microbubbles do not interfere with the injection needle piercing the septum and do not affect sealing of the septum after the withdrawal of the needle due to the small size of the microbubbles.

Although the invention herein has been described with reference to particular embodiments, it is to be understood that these embodiments are merely illustrative of the principles and applications of the present invention. For example, although the present invention is described primarily in connection with a mammary tissue expander, it is to be understood that the inventive concept is similarly applicable to any inflatable mammary implant, such as an adjustable permanent implant, or any other expandable implant. It is therefore to be understood that numerous modifications may be made to the illustrative embodiments and that other arrangements may be devised without departing from the spirit and scope of the present invention as defined by the appended claims.

What is claimed is:

1. A mammary implant comprising:
   a shell having an anterior face and a posterior face;
   an injection element coupled to the anterior face of the implant and adapted to receive therethrough an injection device for injecting fluid into said shell; and
   an injection marker zone that forms part of the injection element,
   wherein the injection marker zone is comprised of a material having ultrasonically detectable markers incorporated therein, wherein the markers are a plurality of microcavities that are located relative to the injection element so that, when ultrasonically detected, such detection indicates a location of the injection element and wherein the plurality of microcavities are embedded within a material comprising at least a part of said injection element.

2. The mammary implant according to claim 1, wherein the plurality of microcavities each have a size less than or equal to 200 microns.

3. The mammary implant according to claim 2, wherein the plurality of microcavities are filled with gas.

4. The mammary implant according to claim 3, wherein the gas is air.

5. The mammary implant according to claim 3, wherein the gas is selected from the group consisting of air, nitrogen, carbon dioxide, and argon.

6. The mammary implant according to claim 1, wherein the plurality of microcavities have a density of at least 1000 microcavities per $cm^2$.

7. A mammary implant comprising:
   a shell having an anterior face and a posterior face;
   an injection element coupled to the anterior face of the implant and adapted to receive therethrough an injection device for injecting fluid into said shell; and
   an injection marker zone that is configured to substantially surround said injection element, and forms part of the shell;
   wherein the injection marker zone is comprised of a material having ultrasonically detectable markers incorporated therein, wherein the markers are a plurality of microcavities that are located relative to the injection element so that, when ultrasonically detected, such detection indicated a location of the injection element.

8. The mammary implant according to claim 7, wherein the injection marker zone has a substantially circular outer shape.

9. The mammary implant according to claim 7, wherein the injection marker zone has a substantially rectangular outer shape.

10. The mammary implant according to claim 7, wherein the injection marker zone forms part of the outer shell, and wherein the plurality of microcavities are incorporated within said shell.

11. The mammary implant according to claim 10, wherein the shell is comprised of silicone.

12. An inflatable implant comprising:
   a shell having an anterior face and a posterior face;
   an injection element coupled to the anterior face of the implant and adapted to receive therethrough an injection device for injecting fluid into said outer shell; and
   an injection marker zone forms part of the injection element,
   wherein the injection marker zone is positioned relative to the injection element so as to identify a location of said injection element, wherein the injection marker zone is comprised of a material having incorporated therein a plurality of gas filled microcavities each having a size less than or equal to 200 microns and wherein the plurality of microcavities are embedded within a material comprising at least a part of said injection element.

* * * * *